US005829971A

United States Patent [19]
Razdolsky et al.

[11] Patent Number: 5,829,971
[45] Date of Patent: Nov. 3, 1998

[54] OSTEODISTRACTION DEVICE FOR USE IN MANDIBULAR DISTRACTION OSTEOGENESIS AND A METHOD OF MAKING THE DEVICE

[76] Inventors: Yan Razdolsky, 600 Lake Cook Rd., Suite 150, Buffalo Grove, Ill. 60089; Patrick Driscoll, 203 E. Olive, Prospect Heights, Ill. 60070

[21] Appl. No.: 803,634

[22] Filed: Feb. 21, 1997

Related U.S. Application Data

[63] Continuation-in-part of Ser. No. 606,033, Feb. 22, 1996, Pat. No. 5,735,688, which is a continuation-in-part of Ser. No. 606,037, Feb. 22, 1996, Pat. No. 5,775,907, which is a continuation-in-part of Ser. No. 606,039, Feb. 22, 1996, Pat. No. 5,622,493, said Ser. No. 606,037, is a continuation-in-part of Ser. No. 222,579, said Ser. No. 606,039, is a continuation-in-part of Ser. No. 222,579, Apr. 14, 1994, Pat. No. 5,599,183.

[51] Int. Cl.$^6$ ........................................................ A61C 3/00
[52] U.S. Cl. ......................................................................... 433/7
[58] Field of Search .................................... 433/7, 18, 24

[56] References Cited

U.S. PATENT DOCUMENTS

| | | |
|---|---|---|
| 1,005,010 | 10/1911 | Farnsworth . |
| 1,096,195 | 5/1914 | Roberts . |
| 1,304,721 | 5/1919 | Young . |
| 1,369,665 | 2/1921 | Johnson . |
| 1,520,809 | 12/1924 | Cohen . |
| 1,705,504 | 3/1929 | Sorensen . |
| 2,221,108 | 11/1940 | Rathbun . |
| 2,322,380 | 6/1943 | Mosley, Jr. . |
| 2,773,303 | 12/1956 | Tirone . |
| 3,277,576 | 10/1966 | Kraft . |
| 3,385,540 | 5/1968 | Biederman . |
| 4,017,973 | 4/1977 | Nelson . |
| 4,070,011 | 1/1978 | Glesser . |
| 4,174,570 | 11/1979 | Schwartz . |
| 4,358,269 | 11/1982 | Hay et al. . |

(List continued on next page.)

FOREIGN PATENT DOCUMENTS

| | | |
|---|---|---|
| 2 267 740 | 11/1975 | France . |
| 24 40 856 | 3/1976 | Germany . |
| 365993 | 1/1973 | U.S.S.R. . |
| 995760 | 2/1983 | U.S.S.R. . |

OTHER PUBLICATIONS

S. Widner, M.S. Bleek, S. Lupe, A Comparison of Nerve Grafting within and Lateral to Bone Grafts in Dogs, Section 1112.
Professor Gravrial A. llizarov, M.D. The Principles of the Ilizarov Method, Bulletin of the Hospital for Joint Diseases Orthopaedic Institute, vol. 48, No. 1, 1988, pp. 1–11.
Clifford C. Snyder, M.D. et al., Mandibular Lengthening by Gradual Distraction (Preliminary Report), Plastic and Reconstructive Surgery, vol. 51, No. 5, pp. 506–508.
Peter D. Costantino, M.D. et al., Segmental Mandibular Regeneration by Distraction Osteogenesis, Arch Otolaryngol Head Neck Durg., vol. 116, May 1990, pp. 535–545.
Nolan S. Karp, M.D. et al., Bone Lengthening in the Craniofacial Skeleton, Annals of Plastic Surjury, vol. 24, No. 3, Mar. 1990, pp. 22–28.
Pro Lab Services, Functionals, Brochure with handwritten page No. 3–9.
Michael S. Block, D.M.D. et al., Changes in the Inferior Alveolar Nerve Following Mandibular Lengthening in the Dog Using Distraction Osteogenesis, American Association of Oral and Maxillofacial Surgeons, pp. 652–660.

*Primary Examiner*—Nicholas D. Lucchesi
*Attorney, Agent, or Firm*—Wenderoth, Lind & Ponack, L.L.P.

[57] ABSTRACT

An oral osteodistraction device has first and second sets of engagement members adapted to be attached to at least teeth of respective opposite lateral sides of one of the bones of the jaw. A first expander assembly is attached to the first set of engagement members, the first expander assembly having at least one expandable screw device. A second expander assembly is attached to the second set of tooth engagement members, the second expander assembly also comprises at least one expandable screw device.

13 Claims, 4 Drawing Sheets

U.S. PATENT DOCUMENTS

| | | |
|---|---|---|
| 4,370,129 | 1/1983 | Huge . |
| 4,433,956 | 2/1984 | Witzig .......................................... 433/7 |
| 4,468,196 | 8/1984 | Keller ..................................... 433/7 X |
| 4,482,318 | 11/1984 | Förster . |
| 4,507,084 | 3/1985 | Blechman et al. . |
| 4,571,177 | 2/1986 | Dahan . |
| 4,571,178 | 2/1986 | Rosenberg ............................. 433/7 X |
| 4,573,914 | 3/1986 | Nord . |
| 4,579,528 | 4/1986 | Staubli . |
| 4,676,745 | 6/1987 | Zurita . |
| 4,713,000 | 12/1987 | Rosenberg ............................. 433/7 X |
| 4,723,910 | 2/1988 | Keller . |
| 4,741,696 | 5/1988 | Celtin . |
| 4,802,849 | 2/1989 | Collins, Jr. . |
| 4,976,614 | 12/1990 | Tepper . |
| 5,007,828 | 4/1991 | Rosenberg . |
| 5,022,855 | 6/1991 | Jeckel ....................................... 433/18 |
| 5,133,659 | 7/1992 | Shilliday . |
| 5,167,499 | 12/1992 | Arndt et al. . |
| 5,167,500 | 12/1992 | Miura . |
| 5,364,396 | 11/1994 | Robinson et al. . |
| 5,645,422 | 7/1997 | Williams ..................................... 433/7 |

OSTEODISTRACTION DEVICE FOR USE IN MANDIBULAR DISTRACTION OSTEOGENESIS AND A METHOD OF MAKING THE DEVICE

This is a Continuation in Part of U.S. patent application Ser. No. 08/606,033, now U.S. Pat. No. 5,735,688 Ser. No. 08/606,037 now U.S. Pat. No. 5,775,907 and Ser. No. 08/606,039, now U.S. Pat. No. 5,622,493 all filed on Feb. 22, 1996 which latter two are each continuations-in-part of 08/222,579, filed Apr. 14, 1994, and now U.S. Pat. No. 5,599,183.

BACKGROUND OF THE INVENTION

The present invention relates generally to the correction of deficiencies in mandibular growth. More specifically, the present invention relates to a device for mandibular distraction osteogenesis the (lengthening of the lower jaw by stretching) for correcting deficiencies in mandibular length.

Deficiencies in mandibular growth which lead to characteristic protrusions of the maxillary teeth and deficiencies of the chin are quite common in American and Northern European populations. Data from recent large scale U.S. Public Health Service surveys of the occlusion of children and youth ages 6 through 10 indicate that about 20 percent of the U.S. population has mandibular deficiency, and about 5 most of the 20 percent of the total U.S. population has skeletal mandibular deficiency (deficiency in the growth of the lower jaw) so severe that the only way to correct such deficiency is to perform a total mandibular (lower jaw) resection (osteotomy) and to advance the lower jaw to a more favorable forward position.

A total mandibular osteotomy, or a sagittal split osteotomy, is a major surgical procedure that can have many complications. In this procedure, as illustrated in FIG. 1, a human mandible is split at opposite points on the mandible. The forward part of the mandible is then brought apart from the rearward part and stabilized with either: (1) screws at point S as labeled in the figure (the forward part F is indicated in FIG. 1 by the arrows A as having been moved; this procedure is used less commonly now than in previous years due to the inherent difficulty in positioning of three loose parts of the mandible correctly during the surgery) or (2) splinting of the broken lower jaw to a prefabricated interocclusal splint which is secured to the upper jaw and allowing it to heal for approximately 2 months (during which the patient cannot open his/her mouth, cannot communicate or function and is fed through a straw).

This procedure cuts the bone marrow, and thus could be detrimental to the inner nerves and blood vessels of the mandible.

In addition, a total mandibular osteotomy can involve the complications of bleeding, obstruction of the airway, possible infection, neurological problems such as possible paralysis of the inferior alveolar nerve and loss of sensation to the lip, failure of intermaxillary fixation (stabilization of the mandible after surgery), relapse-movement of the lower jaw in the direction from which it was advanced, and possible displacement of the temporo-mandibular jaw joints during the surgery.

Needless to say, such surgery requires a hospital stay, is very expensive and many patients are reluctant to agree to this. Further, total treatment time is on the order of 30 months.

The other 15 percent of mandibular deficiencies are less severe, and if they are caught early, during the pubertal growth stage, are amenable to conventional orthodontics (braces) or a combination of orthodontics and functional appliance treatment. However, functional appliances are of most benefit to a patient when the patient is undergoing body and jaw growth, and cannot benefit adult (non-growing) patients.

One other prior art surgical technique bears mention. A process of lengthening human long bones (limbs, arms, etc.) by distraction osteogenesis has been utilized for the past 40 years. This process was designed by a Russian surgeon, Dr. Gavriel A. Ilizarov. The principles of the method of Dr. Ilizarov are presented in an article based on a speech delivered by Dr. Ilizarov on Oct. 30, 1987 at the annual Scientific Program of the Alumni Association and material presented by Dr. Ilizarov at a three day international conference on the Ilizarov techniques for the management of difficult skeletal problems. His technique is being widely used by orthopedic surgeons throughout the United States and the world.

The present inventors have arrived at a method of mandibular distraction osteogenesis, a mandibular distraction device for use in mandibular distraction osteogenesis and attachments for a mandibular distraction device as reflected in each of U.S. application Ser. Nos. 08/606,033, 08/606,037 and 08/606,039, each filed Feb. 22, 1996. The present invention reflects certain advances and improvements over the methods and apparatus of those applications. As such, the following will not repeat most of what is set forth in those applications, but will be addressed to such improvements and modifications. Accordingly, each of those applications is incorporated herein by reference to avoid repeating their description.

SUMMARY OF THE INVENTION

The objective of the present invention is to provide an appliance or device suitable for distraction osteogenesis that is applicable to the five percent of severe cases requiring surgery as well as to the less severe 15 percent of cases if those cases have missed their opportunity for orthodontic/functional correction during their pubertal growth years. Distraction osteogenesis is, by definition, the process of generating new bone by stretching. Thus, it is the more specific object of the present invention to provide a device for generating new mandibular bone by stretching the mandible, while orthodontically lengthening the mandible and minimizing the extent of the conjunctive lower jaw surgery.

The objectives of the present invention are met by a device used in a method of mandibular distraction osteogenesis. This method involves performing corticotomy surgery, where only the cortex of the mandible is cut, leaving all bone marrow, nerve and blood vessels intact, at two points on opposite sides of the mandible. The device is an expandable distraction device attached to the teeth of the mandible on opposite sides of the two points of the corticotomy surgery, and the expandable distraction device is then periodically expanded until a desired mandibular length is attained.

An oral osteodistraction device according to the present invention has first and second sets of engagement members that are adapted to be attached to at least some of the teeth of respective opposite lateral sides of one of the bones of the jaw. The bone could be the mandible or the maxilla. A first expander assembly is attached to the first set of engagement members and includes at least one expandable screw device. A second expander assembly is attached to the second set of tooth engagement members and also has at least one expandable screw device. Receptors and connectors as described in the above-referenced U.S. patent applications are adapted for us with the engagement members and expander assemblies.

In accordance with a first feature according to the improvements of the present application, only one crown need be provided on each side of each corticotomy site. Additional support is provided by a wire extension from that crown to an adjacent tooth. Preferably the adjacent tooth is the tooth closest to the corticotomy site. Furthermore, only a single expandable screw device is necessary for each side of the appropriate part of the jaw, located on the outside for access purposes.

The wire extensions allow the distraction device to be more open and accessible.

During construction of the distraction device, the receptors are soldered to the crowns. This soldering is preferably done through the use of a paralleling tool which maintains the receptors on one side of the bone of the jaw parallel with respect to each other. This properly aligns the receptors so that the expandable screw device can be properly removed and attached.

The corticotomy site could also be the rear-most point along the mandible or maxilla. In this instance, there are no teeth on one side of the corticotomy site for connection with the device. As such, a bone plate is attached to the bone by bone screws. The receptor is soldered to the bone plate as with the crowns.

A vertical hole extends through the receptors. This vertical hole is used not only for alignment of the receptors by the use of the paralleling tool, but can only be used for connection between the receptors and connectors. When the connectors are mounted on the receptors in assembly of the device, they can be maintained thereon by a wire extending through the vertical holes so as to hold the connectors on the receptors. Alternatively, a spring clip could be used.

According to the present invention, the invention also contemplates an assembly kit made up of the components described above for constructing a mandibular distraction device and the method of making the mandibular distraction device, it being understood that the mandibular distraction device is a custom made device made by a doctor from the components for a particular patient for the purposes of conducting the above-described procedure.

Through the employment of mandibular distraction osteogenesis according to the present invention, and the use of the mandibular distraction device according to the present invention, a number of significant advantages may be achieved. As noted above, the invention will orthodontically lengthen the mandible while minimizing the extent of the conjunctive lower jaw surgery. Only corticotomy is employed.

Further, the invention will improve the facial profile by advancing or lengthening the deficient mandible. This will improve the lip balance, lip competence, and lip seal. This will also help to eliminate mouth breathing pattern problems. Further, incisor guidance and function will be established.

The invention will also reduce the orthodontic-surgical treatment time. Treatment time can be expected to be reduced to on the order of 12 months, instead of 30 months as with the prior art sagittal split osteotomy surgery.

The invention will also bring the mandible forward, thus bringing the tongue forward and diminishing chances for obstructive sleep apnea or snoring. Such correction will also help to prevent class II mandibular deficiency/malocclusion. The invention will help to correct unilateral cross bites and the mandibular midline.

Further, the invention will minimize damage to the periosteal and endosteal blood supply by performing a corticotomy only, rather than a complete osteotomy as is now performed with the sagittal split osteotomy surgery. This will minimize swelling and post-surgical complications, and requires no hospital stay and could be done on an outpatient basis. Furthermore, the fact that the expansion screw assemblies are detachable from the receptor assemblies means that the orthodontist will generally not need to be present during surgery. The precise pre-alignment will have been done during fitting in the office.

Further, the procedure will be far less expensive than the conventional mandibular osteotomy surgery. Patient costs for the procedure are lower than the costs associated with prior art methods such as the sagittal split osteotomy surgery. Obviously this will tend to lower health care costs in general, which is a great concern at this time.

Other significant advantages result to the benefit of the patient. The procedure according to the present invention results in less pain to the patient than the prior art procedure. The recovery period after completion of the procedure is on the order of two to three days, rather than two months as with other methods. The jaw of the patient does not have to be wired shut for two months, and the patient is able to return to work within one week, as opposed to eight weeks with other methods. Thus it is clear that the psychological impact of the procedure on the patient will be significantly reduced as compared with the impact of the prior art methods.

BRIEF DESCRIPTION OF THE DRAWINGS

The present invention will be described in detail below with reference to the accompanying drawings, in which.

DETAILED DESCRIPTION OF THE PREFERRED EMBODIMENTS OF THE INVENTION

A detailed description of the improvements over the above-referenced U.S. patent applications will now be presented with reference to the accompanying drawing figures.

Figure 1:
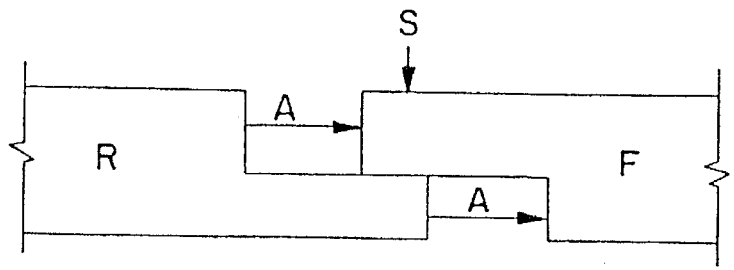
FIG. 1 is a schematic drawing illustrating sagittal split osteotomy surgery.
Figure 2:
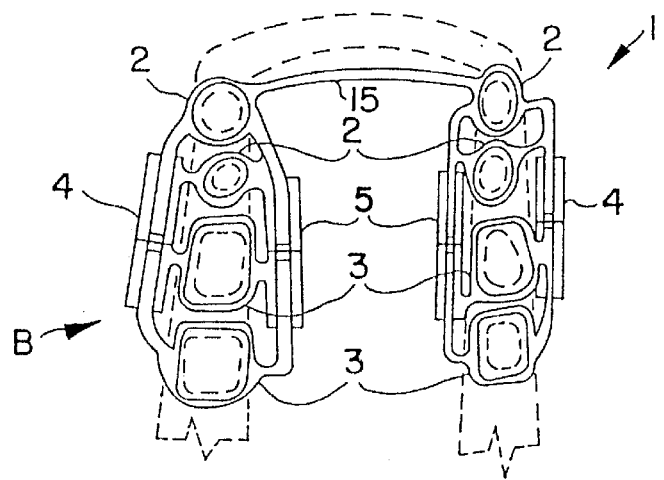
FIG. 2 is a top view of a mandibular distraction osteogenesis device according to the present invention.
Figure 3:
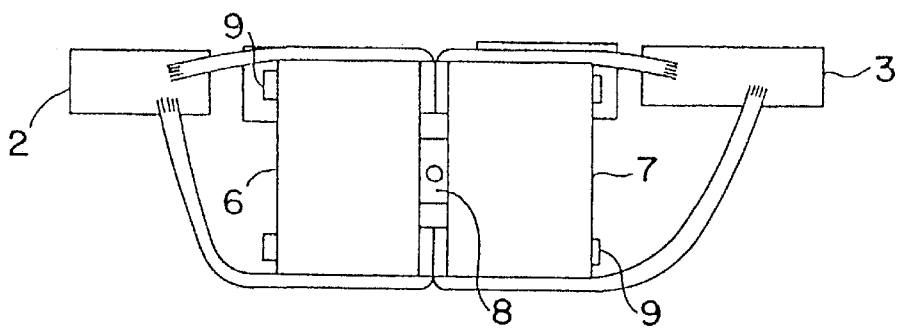
FIG. 3 is a side view of a portion of the mandibular distraction device as seen in the direction of arrow B of FIG. 2.
Figure 4:
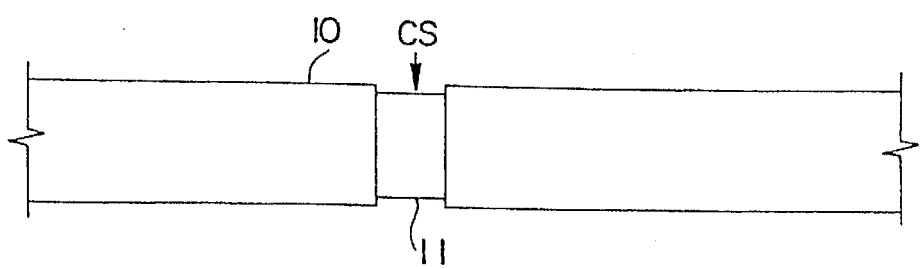
FIG. 4 is a schematic representation of corticotomy surgery.

Turning to FIG. 2, there is illustrated a mandibular distraction osteogenesis device 1 as described in the above-referenced U.S. patent applications incorporated herein by reference and usable in distracting the mandible. Initially, the device 1 includes a plurality of crowns (or bands, collectively also referenced as tooth engagement members) for placement on the teeth of the mandible of a patient that is to undergo distraction osteogenesis. The tooth engagement members of the present invention are preferably crowns, but it should be recognized that bands could also be employed instead of crowns; the description will primarily discuss crowns. In FIGS. 2 and 3, while the description references crowns, the illustration in these figures is not meant to be indicative of any particular type of crown but to be simply a generic description of a crown or band for purposes of illustrations.

Preferably there are provided a total of eight crowns, with two bicuspid and two molar orthodontic crowns being provided for each side of the mandible, as illustrated in FIG. 2. The crowns are indicated by reference numbers 2 for the bicuspid crowns and reference numbers 3 for the molar crowns. The mandible and the relevant teeth are schematically illustrated by a dashed line in FIG. 2.

One universal expansion screw 4 is soldered onto each buccal (cheek) side of the crowns and one universal sliding tube device 5 is soldered onto each lingual (tongue) side of the crowns for each side of the mandible. One universal expansion screw 4 and one sliding tube 5 is thus placed on each side of each set of crowns. As can be seen from FIG. 2, the universal expansion screws thus extend along the sides of the crowns and have suitable portions thereof soldered to the respective crowns. The universal expansion screws 4 are expandable to distract a forward portion of the mandible, the upper portion as seen in FIG. 2, from a rearward portion of the mandible by separating the bicuspid bands 2 from the molar bands 3.

More specifically, and referring to FIG. 3, each universal expansion screw 4 has two halves 6 and 7 separable from each other by a screw mechanism 8. The screw mechanism 8 is a suitable mechanism rotatable between the universal expansion screw halves 6 and 7 to separate the halves from each other, such as a right and left hand threaded shaft extending into and engaging with corresponding threads in the halves 6 and 7. Suitable guide rods 9 can also extend through the halves 6 and 7 to guide the separation of the halves 6 and 7 from each other. As can be seen, suitable connecting portions are provided for connecting the halves 6 and 7 to the respective bands 2 and 3. Such connecting portions can take the form of appropriate metal wires or bars. The universal expansion screw 4 can be of the type illustrated in U.S. Pat. No. 4,482,318, for example, or could be of the type shown in U.S. Pat. No. 4,571,177, suitably adapted to the present situation. These patents are incorporated herein by reference.

By the above construction there is formed two separate portions of the mandibular distraction device 1, one portion being located on each side of the mandible. These portions are preferably connected to each other by a suitable connecting wire or bar 15, as illustrated in FIG. 2. However, note that in place of the connecting wire or bar 15, an additional, smaller, universal expansion screw 4 could be provided and incorporated into the device 1, the universal expansion screw connecting the two sides of the device 1 at the forward portions thereof in order to allow for lateral mandibular expansion, in addition to mandibular distraction or elongation.

As can be seen from FIG. 2, the bicuspid crowns 2 on each side of the mandible are connected to the forward portions or halves 6 of the universal expansion screws 4, and the molar crowns 3 are connected to the rear portions or halves 7 of the universal expansion screws 4. Thus, a unitary forward portion is expansible in a forward direction relative to two separate lateral portions on opposite sides of the mandible for elongation or distraction of the mandible.

While the above described distraction device 1 simply solders the expansion screws and sliding tubes 5 to the crowns 2 and 3, it is preferred that specific attachments be employed for this purpose, as is described in the above-referenced U.S. patent applications incorporated herein by reference. The specific nature and use of these attachment will not be further described herein, as they have been thoroughly discussed above, except with respect to modifications thereof.

The method of distraction osteogenesis described in the above-referenced U.S. patent applications incorporated herein by reference will also not be repeated, except with respect to modifications thereof. Note this method contemplates use of the laboratory instrument discussed in U.S. Pat. No. 5,559,183, also incorporated herein by reference.

With the present invention, the mandible can be distracted at a rate of 1 mm per day until the proper mandibular length is obtained. Recommended distraction is at a rate of 0.5 mm to 1.0 mm per day until the proper length is obtained. The appliance is left in place two days for each 1 mm of expansion in order to allow for the complete bony union after expansion. There may be differential expansion between the left and right sides in order to maintain expansion along the centerline of the mandible.

In FIG. 2 above four expander assemblies 4 were illustrated for use with the distraction device, one expander assembly being disposed on each side of each line of tooth engaging members 2 and 3. A screw assembly does not need to be on each side in accordance with the above discussion, and could be replaced by a simple slide assembly. However, the slide assembly could also be removed entirely. That is, it would be sufficient in terms of the proper functioning and strength of the distraction device as a whole if a single screw assembly was employed on each side of the distraction device, with no other support on the opposite side of the tooth line such as was before provided by the slide assembly. Thus, for example looking at FIG. 2, the two inside expander assemblies 4 could be removed entirely, with no other support on that side, and sufficient strength and support be maintained.

In another variation according to the present invention, it is particularly noted that the engagement members are not limited to eight tooth engagement members as illustrated in FIG. 2. That is, instead of having two tooth engagement members on each side of the corticotomy site on each side of the jaw as illustrated in FIG. 2, a single tooth engagement member could be provided on each side of the corticotomy site. In this instance, it is preferred that additional support be provided. This will be explained in the following.

Figure 5:
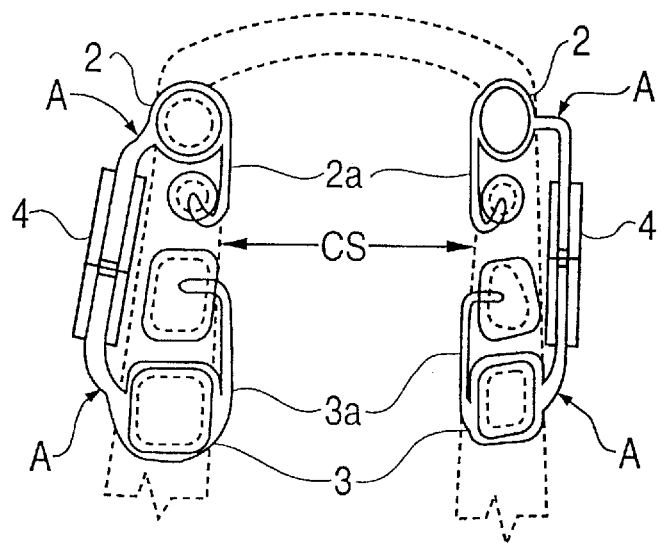
FIG. 5 is a top view of an osteodistraction device according to the present invention, representing a modification from FIG. 2.

This arrangement is illustrated in FIG. 5. This is clearly a modification from FIG. 2, and serves to demonstrate the simplification that can take place. The corticotomy site is designated by CS. There are no crowns or bands on either side of the corticotomy site, the adjacent teeth being left uncapped. Rather, the next teeth in line have crowns 2 and 3 thereon. In order to provide sufficient support, wire extensions 2a and 3a extend to the adjacent teeth. Expandable screw assemblies 4 or sliding tube assemblies are not provided on the inside portion. Nonetheless, this allows for sufficient support. The locations designated by A are the location where the attachments would be soldered, clearly. Thus, a much more open and simple arrangement overall can be provided. Use of the wire extensions will be explained in more detail below.

Figure 6:
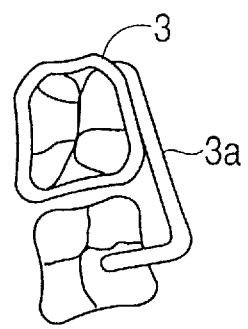
FIG. 6 illustrates the use of wire attachments for support.

For example, a molar cap 3 is illustrated in FIG. 6 on top of a molar, adjacent to an un-capped tooth, for example another molar. A wire or extension 3*a* can extend to the adjacent tooth, extending along the side thereof in close proximity thereto, and up and into the center portion of the tooth to provide additional support beyond the single crown or cap. When this arrangement is used, it is preferred that the tooth adjacent to the corticotomy site be uncapped and have the wire 3*a* extending thereto, and that the cap be placed on the next tooth in line. Thus, an arrangement could be provided only employing a total of four molar caps 3, for example, each having a respective wire or extension 3*a* to the teeth adjacent to the corticotomy site. Thus, if reference is again made to FIG. 5, the two inner caps 2 and 3 on each side of the jaw are replaced by wire extensions leading from the outer caps 2 and 3. This is combined with the removal of the interior expander assemblies 4 to provide a very open and simple arrangement, yet one having sufficient strength in operation.

Figure 8:
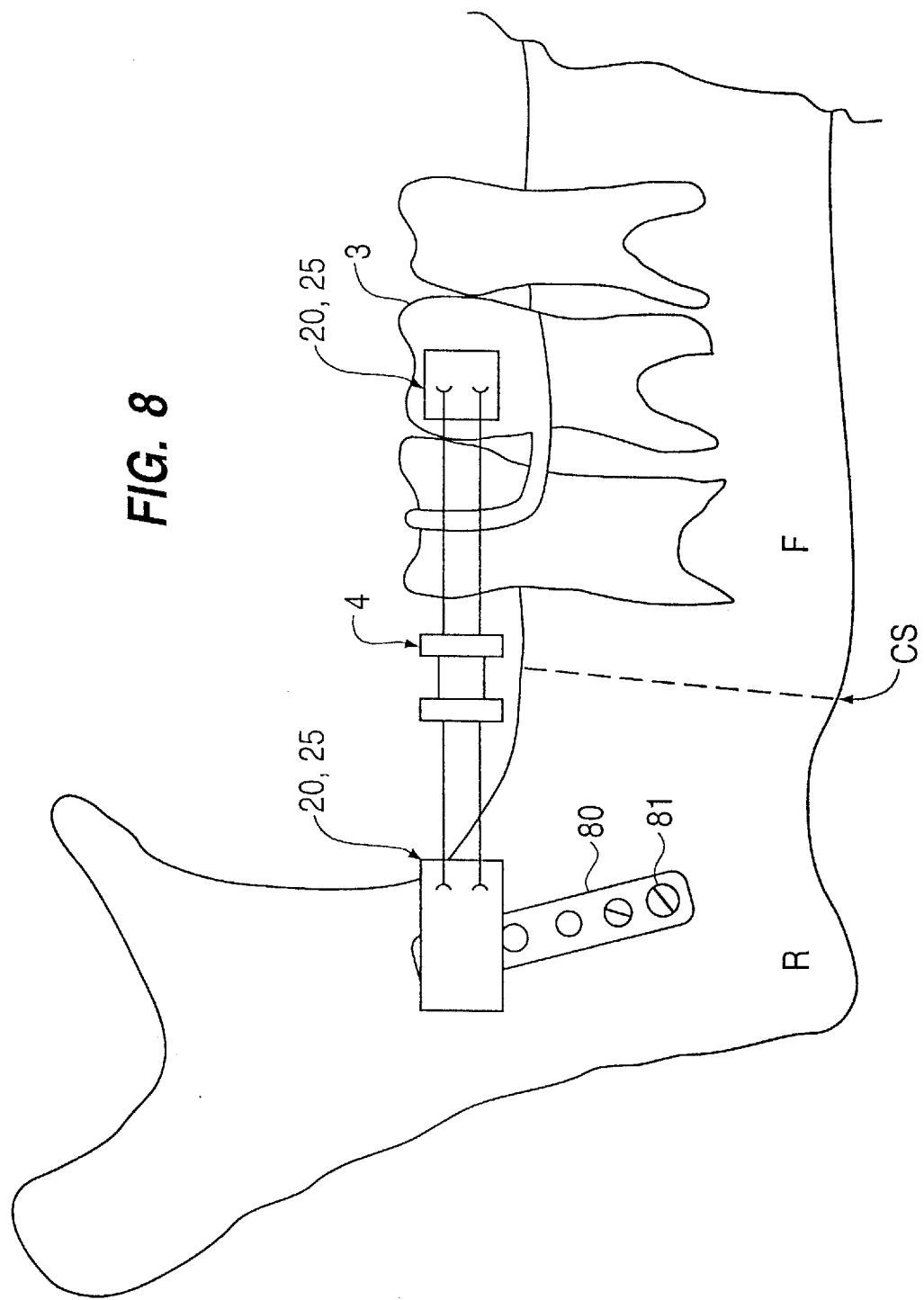
FIG. 8 is a schematic illustration of another embodiment of the distraction device according to the present invention as applied to a mandible.

Referring now to FIG. 8, an alternative arrangement of a distraction device is illustrated. In this arrangement, while only one side of the jaw is illustrated, a similar arrangement is provided for the other side of the jaw.

As can be seen from FIG. 8, the concept here is to perform corticotomy at a site rearward of the last tooth along the tooth line. This involves not having to make the corticotomy between two teeth. The extension of the mandible thus takes place rearward of the last tooth, in some respects simplifying the overall operation.

The components necessary for this device can be similar to those above, or can be according to the preferred arrangement in FIG. 8. In FIG. 8, on one side of the mandible, on the forward portion F, a single molar crown 3 is provided. A wire attachment 3*a* extends from this crown 3 to the adjacent tooth. As discussed above, the wire extension 3*a* extends toward the corticotomy site CS. Rearward of the corticotomy site, a bone plate 80 is attached by bone screws 81 at a suitable location for purposes of anchoring the attachments used in connecting the screw expander assembly 4. A suitable receptor 25 is welded to the bone plate 80, and a suitable receptor 25 is welded to the crown 3, as discussed above. A screw expander assembly is connected to the connectors 20 as also discussed above, the connectors 20 being connectable with the receptors 25 for use in distraction.

The distraction procedure discussed above can also be performed with the maxilla. In a preferred arrangement, the preformed stainless steel crowns are placed over the second molars on the first bicuspids, but other combinations will also work, for example using the second bicuspid and the first molar, etc. The second molar and the first bicuspid are preferred, because the osteotomy is performed between the second bicuspid and the first molar and the crowns on the second molars and the first bicuspid thus do not interfere with the surgery (osteotomy).

In maxillary distraction, the stainless steel crowns could be placed anywhere, depending on the area of the osteotomy and the desired amount of distraction.

Figure 7:
FIG. 7 illustrates a paralleling tool.

As discussed above, in the method according to the present invention a rubber base impression is taken of the mouth with the stainless steel crowns in place. The crowns are then removed from the mouth and placed in the impression, pinned into position, and the impression is poured up with green or any heat resistant dental stone or material. A model is then produced with the stainless steel crowns on it. After this step, the removable attachments are soldered to the stainless steel crowns. In order to maintain the attachments aligned, the vertical holes 57 in the attachments come into play. That is, a paralleling tool 90 as illustrated in FIG. 7 has two parallel pins thereon inserted into the holes 57 of the two receptors used for a particular side of the jaw. It is very important that these receptors be maintained parallel during soldering so that the expander assembly 4 can be properly attached and detached. Thus the paralleling tool 90 is used to align the attachments during soldering. Note that the pins 91 are adjustable along the shaft of the tool for different desired spacings between the respective attachments.

The model having the attachments thereon is then placed into a laboratory tool, for example the tool discussed above with respect to U.S. Pat. No. 5,559,183. This tool is used to solder the expanders bilaterally correctly into the proper three dimensional position as determined from the skull, panoramic X-rays and study models or other diagnostic materials as available.

Once the expanders are soldered, two separate orthodontic wires as wires 3*a* illustrated in FIG. 6 are soldered on the lingual surfaces of the mandibular second molar and mandibular first bicuspid (in this example) and adapted to the occlusal surfaces of the mandibular first molar and the second bicuspid. The wire that is adapted to the first molar and the second bicuspid will later be bonded to the respective teeth in the mouth.

The distraction device is now ready to be cemented into the patients mouth. The device or appliance is cemented via the crowns to the second molars and the first bicuspids (in this example). The lingual wires which were soldered to the lingual surface of the second molar and first bicuspid crowns are now bonded to the occlusal surface of the mandibular first molar and the second bicuspid. The two expanders 4 are then removed by means of the removable attachments in order to allow the osteotomy surgery to take place. The expanders are reattached by the attachments after surgery and are secured in place with orthodontic or surgical wire (as an alternative to the above-referenced glue or locking) through the vertical holes 57 in the attachments.

Figure 9:
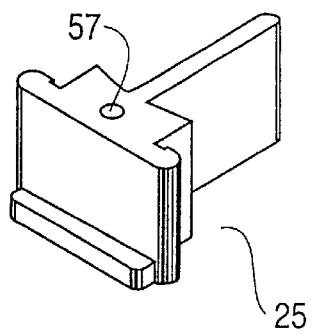
FIG. 9 is a perspective view of a receptor according to the present invention.
Figure 10:
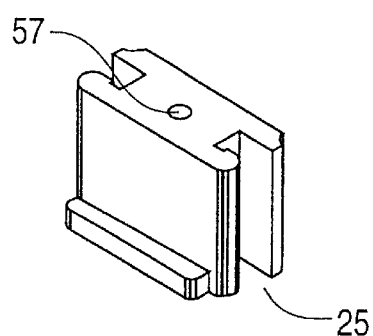
FIG. 10 is a perspective view of another embodiment of a receptor according to the present invention.
Figure 11:
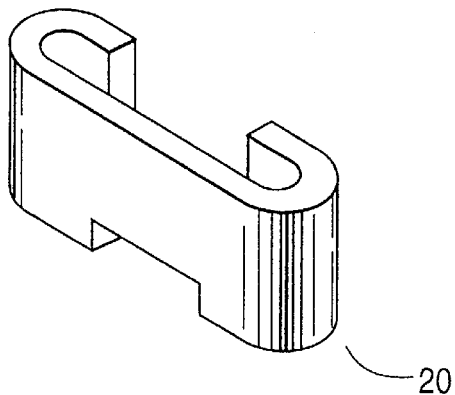
FIG. 11 is a perspective view of a connector according to the present invention.
Figure 12:
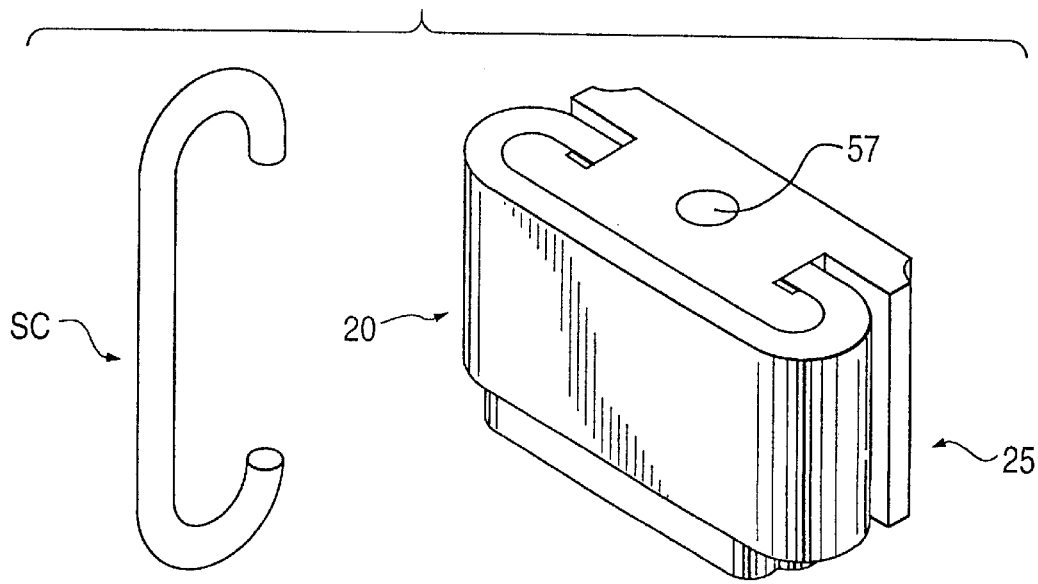
FIG. 12 is a perspective view of an assembled receptor and connector together with a spring clip for holding them together.

FIGS. 9 and 10 illustrate two additional embodiments of receptors. FIG. 11 illustrates an additional embodiment of a connector 20. The combination of a receptor and connector is illustrated in FIG. 12 along with a spring clip SC. The use of these devices will be apparent from the above-referenced U.S. patent applications incorporated herein by reference.

While a wire is used, in the above described embodiment, to connect the receptors and the connectors 25 and 20, a locking device could be incorporated into the attachments. For example, a releasable coupling between the receptors and connectors could be provided. As an alternative, clips could also be provided for simply clipping the connectors and receptors. In terms of mechanical play, however, either adhesive or twisted alloy wire extending through the vertical holes 57 is preferred. However, hardened stainless wire clips SC (FIG. 12) for retaining the receptors and connectors after surgery could be contemplated if crimped tight with surgical pliers. Also, the orthodontic wire could be used to secure the expander in place after surgery, and in addition, it could be glued or bonded over for additional stability.

While preferred embodiments of the present invention have been described above in some particularity, the scope of the present invention should not be limited thereby, as various modifications thereof will be apparent to those of skill in the art.

I claim:

1. An oral osteodistraction device, comprising:

first and second sets of engagement members adapted to be attached to at least teeth of respective opposite lateral sides of one of the bones of the jaw;

a first expander assembly attached to said first set of engagement members, said first expander assembly comprising at least one expandable screw device; and a second expander assembly attached to said second set of tooth engagement members, said second expander assembly also comprising at least one expandable screw device;

wherein said first and second sets of engagement members have receptors attached thereto, and said first and second expander assemblies have connectors attached thereto that are removably engageable with said receptors; and wherein each of said first and second sets of engagement members comprises at least one tooth engagement member and one bone engagement member, and wherein said first and second expander assemblies are removably attached to said first and second sets of engagement members by receptors fixed to said first and second sets of engagement members and connectors fixed to said first and second expander assemblies, said connectors being removably engageable with said receptors.

2. The distraction device of claim 1, wherein said bone engagement member comprises a bone plate and bone screws for fixing said bone plate to a bone of the jaw, and one of said receptors is fixed to said bone plate.

3. The distraction device of claim 1, wherein said receptors and said connectors are made of stainless steel and soldered to said engagement members and said expander assemblies, respectively.

4. The distraction device of claim 1, wherein each said expandable screw device comprises first and second body portions having aligned threaded holes extending therein and a threaded shaft engaging both said threaded holes.

5. The distraction device of claim 1, wherein each of said first and second expander assemblies comprises a single said expandable screw device on one side of the respective said set of engagement members.

6. An oral osteodistraction device, comprising:

first and second sets of engagement members adapted to be attached to at least teeth of respective opposite lateral sides of one of the bones of the jaw;

a first expander assembly attached to said first set of engagement members, said first expander assembly comprising at least one expandable screw device; and a second expander assembly attached to said second set of engagement members, said second expander assembly also comprising at least one expandable screw device;

wherein said first and second sets of tooth engagement members have receptors attached thereto, and said first and second expander assemblies have connectors attached thereto that are removably engageable with said receptors;

wherein each one of said first and second sets of engagement members has at least two receptors connected therewith in parallel alignment, and each one of said first and second expander assemblies has at least two connectors attached thereto in parallel alignment for connection with respective said receptors; and wherein each one of said first and second sets of engagement members comprises one crown having one of said at least two receptors soldered thereto and a wire extension extending therefrom adapted to engage a tooth and a bone plate having bone screws and another of said at least two receptors soldered thereto, and wherein each one of said first and second expander assemblies comprises an expandable screw device separable at a middle point thereof and having one of said at least two connectors soldered thereto on either side of said middle point.

7. A method of making an oral osteodistraction device, comprising the steps of:

fitting crowns to teeth of a one of a mandible and maxilla to be distracted;

taking an impression of the one of the mandible and the maxilla;

making a model of the one of the mandible and the maxilla such that the model has the crowns thereon;

soldering receptors, which have corresponding connectors that are adapted to be removably connected with respective ones of the receptors, to the crowns such that receptors on each side of the one of the mandible and the maxilla are in parallel alignment; and soldering expander devices to the connectors.

8. The method of claim 7, wherein the receptors are soldered to the crowns while being maintained in parallel alignment by a paralleling tool holding the receptors.

9. The method of claim 7, wherein the expander devices are soldered to the connectors while the connectors are mounted on the receptors and while the receptors and the crowns to which the receptors are soldered are mounted on teeth of the model of the one of the mandible and the maxilla.

10. A kit for assembling an osteodistraction device, comprising:

first and second sets of engagement members adapted to be attached to at least teeth of respective opposite lateral sides of one of the bones of the jaw;

a first expander assembly that is to be attached to said first set of engagement members, said first expander assembly comprising at least one expandable screw device;

a second expander assembly that is to be attached to said second set of engagement members, said second expander assembly also comprising at least one expandable screw device; and receptors adapted to be attached to the first and second sets of engagement members, and connectors adapted to be attached said first and second expander assemblies that are removably engageable with said receptors;

wherein each of said first and second sets of engagement members comprises at least one tooth engagement member and one bone engagement member.

11. The distraction device of claim 10, wherein each of said first and second expander assemblies comprises a single said expandable screw device.

12. The distraction device of claim 10, wherein said bone engagement member comprises a bone plate and bone screws for fixing said bone plate to a bone of the jaw.

13. The distraction device of claim 10, wherein said at least one tooth engagement member comprises a wire extension fixed thereto for extending to and engaging an adjacent tooth.

* * * * *